US012806340B2

(12) United States Patent
Huang et al.

(10) Patent No.: US 12,806,340 B2
(45) Date of Patent: Nov. 24, 2026

(54) INFUSION PUMP AND CONTROL METHOD THEREOF

(71) Applicant: Medcaptain Medical Technology Co., Ltd., Shenzhen (CN)

(72) Inventors: Haoke Huang, Shenzhen (CN); Jun Dong, Shenzhen (CN)

(73) Assignee: Medcaptain Medical Technology Co., Ltd., Shenzhen (CN)

( * ) Notice: Subject to any disclaimer, the term of this patent is extended or adjusted under 35 U.S.C. 154(b) by 471 days.

(21) Appl. No.: 18/395,680

(22) Filed: Dec. 25, 2023

(65) Prior Publication Data

US 2024/0216609 A1 Jul. 4, 2024

(30) Foreign Application Priority Data

Dec. 29, 2022 (CN) ......................... 202211712423.7
Nov. 10, 2023 (CN) ......................... 202311517136.5

(51) Int. Cl.
*A61M 5/168* (2006.01)
*A61M 5/142* (2006.01)

(52) U.S. Cl.
CPC .... *A61M 5/16854* (2013.01); *A61M 5/16831* (2013.01); *A61M 5/142* (2013.01); *A61M 5/168* (2013.01); *A61M 5/16804* (2013.01); *A61M 5/16813* (2013.01); *A61M 5/16863* (2026.08); *A61M 5/16877* (2013.01); *A61M 2205/18* (2013.01)

(58) Field of Classification Search
CPC .................. A61M 5/142; A61M 5/168; A61M 5/16804; A61M 5/161813; A61M 5/16831; A61M 5/16854; A61M 5/16877
USPC ........................................................... 702/85
See application file for complete search history.

(56) References Cited

U.S. PATENT DOCUMENTS

2007/0118405 A1* 5/2007 Campbell ......... A61M 5/14248 705/2
2010/0063765 A1* 3/2010 Carlisle ............. A61M 5/16804 73/1.16
2011/0152697 A1* 6/2011 Kawamura ........ A61B 5/02152 600/485
2014/0180238 A1* 6/2014 Imhof .................... G16H 20/17 604/151
2014/0207057 A1* 7/2014 Zhu .................. A61M 5/14228 604/67
2015/0217044 A1* 8/2015 Blomquist ............. G16H 10/60 700/282

(Continued)

*Primary Examiner* — Paul D Lee
(74) *Attorney, Agent, or Firm* — Jeffrey Pearce

(57) ABSTRACT

The invention provides a control method of an infusion pump and an electronic device that determines identification information and/or consumable information of a target infusion consumable set to the infusion pump; determines, according to the identification information and/or consumable information, a control rule of the infusion pump corresponding to the target infusion consumable; and adjusts according to a preset correction rule, the control rule corresponding to the target infusion consumable. By adjusting the control rule of the target infusion consumable according to the preset correction rule in the invention, the control rule of each target infusion consumable set to the infusion pump can be automatically adjusted, making the manner of calibrating the infusion pump more accurate and convenient.

20 Claims, 7 Drawing Sheets

(56) References Cited

U.S. PATENT DOCUMENTS

| | | | | |
|---|---|---|---|---|
| 2016/0263315 | A1* | 9/2016 | Lau | A61M 5/14244 |
| 2017/0290974 | A1* | 10/2017 | Tsoukalis | A61M 5/1407 |
| 2020/0147303 | A1* | 5/2020 | Lee | A61M 5/14228 |
| 2020/0188588 | A1* | 6/2020 | Estes | G16H 20/17 |
| 2021/0369963 | A1* | 12/2021 | Abal | A61M 5/16831 |

* cited by examiner

INFUSION PUMP AND CONTROL METHOD THEREOF

REFERENCE TO RELATED APPLICATIONS

This application claims priority of Chinese Patent Application No. 202211712423.7, entitled "CALIBRATION METHOD AND DEVICE OF INFUSION PUMP, ELECTRONIC DEVICE AND READABLE MEDIUM" filed with the China National Intellectual Property Administration on Dec. 29, 2022, and Chinese Patent Application No. 202311517136.5, entitled "CONTROL METHOD OF INFUSION PUMP AND INFUSION PUMP" filed with the China National Intellectual Property Administration on Nov. 10, 2023, which are incorporated herein by reference in its entirety.

TECHNICAL FIELD

This invention generally relates to the technical field of infusion pumps, and more particularly, to an infusion pump and a control method thereof.

BACKGROUND ART

Infusion pumps, including syringe pumps, represent intelligent infusion devices widely used for their high precision and reduced reliance on manual intervention. The accuracy of infusion pump calibration directly affects the precision of the infusion process.

In the prior art, the presence of inherent manufacturing and assembly errors within infusion pumps can lead to instances of failed calibration. Currently, the method for calibrating non-compliant infusion pumps typically involves connecting the pump to a specified type of infusion tube. By allowing fluid to flow through the infusion tube into the infusion pump, the pump provides calibration feedback data. Subsequently, according to this calibration data, corresponding components are replaced or calibration parameters are adjusted.

However, the calibration methods in the prior art yield calibration results that lack the desired level of precision.

SUMMARY OF THE INVENTION

The invention provides a control method for an infusion pump and an infusion pump for solving the problem of insufficiently accurate infusion pump calibration.

In a first aspect, the invention provides a control method for an infusion pump, comprising:

determining identification information and/or consumable information of a target infusion consumable set to the infusion pump;

determining, according to the identification information and/or consumable information, a control rule corresponding to the target infusion consumable of the infusion pump;

adjusting the control rule corresponding to the target infusion consumable according to a preset correction rule.

In a second aspect, the invention provides a control method for an infusion pump, comprising:

determining a control rule of a target infusion consumable set to the infusion pump;

operating the infusion pump according to the control rule, and obtaining feedback information of the infusion pump for a preset time period; wherein the feedback information comprises fluid information of the infusion pump;

determining, according to the feedback information, actual consumable information of the target infusion consumable.

In a third aspect, embodiments of the invention provide an electronic device comprising: a processor, and a memory in communication with the processor;

wherein the memory stores computer execution instructions;

the processor executes the computer-executed instructions stored in the memory to implement the control method for an infusion pump described for the first aspect, or to implement the control method of an infusion pump described for the second aspect.

In a fourth aspect, embodiments of the invention provide an infusion pump, comprising: a controller, a drive mechanism, an extrusion member and an infusion consumable; wherein the controller is connected to the drive mechanism, the drive mechanism is connected to the extrusion member in a drive connection, and the extrusion member is disposed on a tube wall of the infusion consumable;

the controller is configured to cause the infusion pump to operate according to an infusion pump control method, the method comprising:

determining identification information and/or consumable information of a target infusion consumable set of the infusion pump;

determining, according to the identification information and/or consumable information, a control rule corresponding to the target infusion consumable of the infusion pump;

adjusting the control rule corresponding to the target infusion consumable according to a preset correction rule.

The invention provides an infusion pump and a method for controlling it, by determining identification information and/or consumable information of a target infusion consumable set to the infusion pump, determining, according to the identification information and/or the consumable information, a control rule pre-set in the infusion pump corresponding to the target infusion consumable, and adjusting, according to a preset correction rule, the control rule corresponding to the target infusion consumable. The invention adjusts the control rule of the target infusion consumable according to the preset correction rule by automatically adjusting the control rule of each target infusion consumable set depending on the infusion pump, making the calibration of the infusion pump more accurate and convenient.

BRIEF DESCRIPTION OF THE DRAWINGS

The accompanying drawings, which are incorporated into and form a part of the specification, illustrate embodiments consistent with the invention and are used in conjunction with the specification to explain the principles of the invention.

Figure 1:
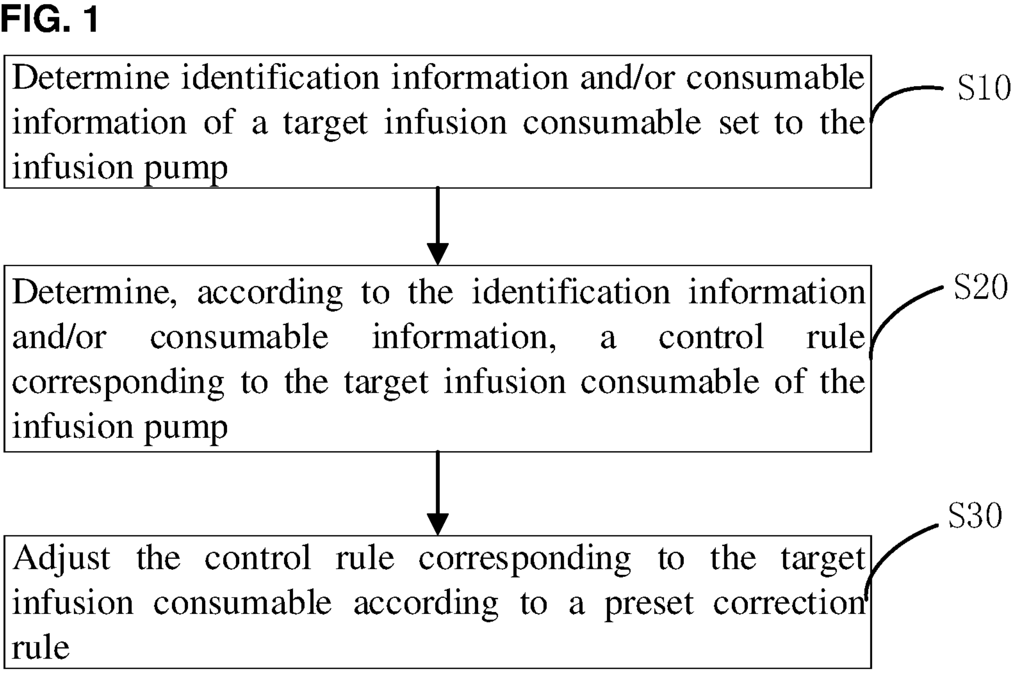
FIG. 1 shows a schematic flowchart of a control method of an infusion pump according to an embodiment of the invention.

Definite embodiments of the invention are illustrated by means of the accompanying drawings described above, and will be described in greater detail later. These accompanying drawings and textual descriptions are not intended to limit the scope of the inventive idea in any way, but rather to illustrate the concepts of the invention for those skilled in the art by reference to particular embodiments.

DETAILED DESCRIPTION

Examples of embodiments will be described herein in detail and are represented in the accompanying drawings. When the following description relates to the accompanying drawings, the same numerals in different accompanying drawings indicate the same or similar elements unless otherwise indicated. The embodiments described in the following example embodiments do not represent all embodiments consistent with the invention. Rather, they are only examples of devices and methods consistent with some aspects of the invention as detailed in the appended claims.

It should be noted that in the description of embodiments of the invention, the terms “inside”, “outside”, and other terms indicative of orientation or positional relationships are according to the orientation or positional relationships shown in the accompanying drawings solely for the purpose of facilitating the description, and are not indicative of, or suggestive of, the fact that a device or member must have a particular orientation, be constructed and operated in a particular orientation, and therefore is not to be construed as a limitation of the invention.

Furthermore, it should be noted that in the description of the embodiments of the invention, unless otherwise expressly provided and limited, the terms “joint” and “connect” are to be understood in a broad sense. For example, it may be a fixed connection, a detachable connection, or an integral connection; it may be a mechanical connection or an electrical connection; it may be a direct connection or an indirect connection through an intermediate medium, and it may be a connection within the two components. For those skilled in the art, the specific meaning of the above terms in the embodiments of the invention may be understood on a case-by-case basis.

The infusion pump and the syringe pump are both intelligent infusion devices capable of accurately controlling the number of drops of infusion or the flow rate of infusion, which are widely used in clinical practice. The infusion pump can greatly improve the accuracy and safety of the infusion process.

Before leaving the factory, infusion pumps need to undergo quality calibration. However, due to inherent processing and assembly errors in the infusion pump, there may be cases where the calibration does not meet the required standards. Currently, the typical method for calibrating unqualified infusion pumps is to connect the pump with a specified type of infusion tube. As the liquid flows through the infusion tube into the infusion pump, the pump provides feedback data for calibration. According to this calibration data, corresponding components may be replaced, or calibration parameters may be adjusted accordingly.

The calibration method in the prior art, which relies on connecting the infusion pump to a specified type of infusion tube, may lead to a limitation where the calibrated pump is only suitable for the specific type of infusion tube used during calibration. When the infusion pump is connected to other types of infusion tubes, the calibration results may not be accurate enough.

In an embodiment, in response to the above technical problems in the prior art, the invention provides a control method, device, apparatus, and a readable medium of an infusion pump, by determining identification information and/or consumable information of a target infusion consumable set to the infusion pump, determining, according to the identification information and/or the consumable information, a control rule preset in the infusion pump that corresponds to the target infusion consumable, and adjusting the control rule corresponding to the target infusion consumable according to the preset correction rule. In this application, the method of adjusting the control rule of the target infusion consumable according to the preset correction rules provides for automatically adjusting the control rule of each target infusion consumable set according to the given infusion pump, which makes the calibration method of the infusion pump more accurate and more convenient.

The technical solution of the invention and how it solves the above-described technical problems are described in detail below with reference to specific embodiments. These following specific embodiments may be combined with each other, whereas, in other embodiments, the same or similar concepts or processes may not be employed. Embodiments of the invention will be described below in conjunction with the accompanying drawings.

Figure 2:
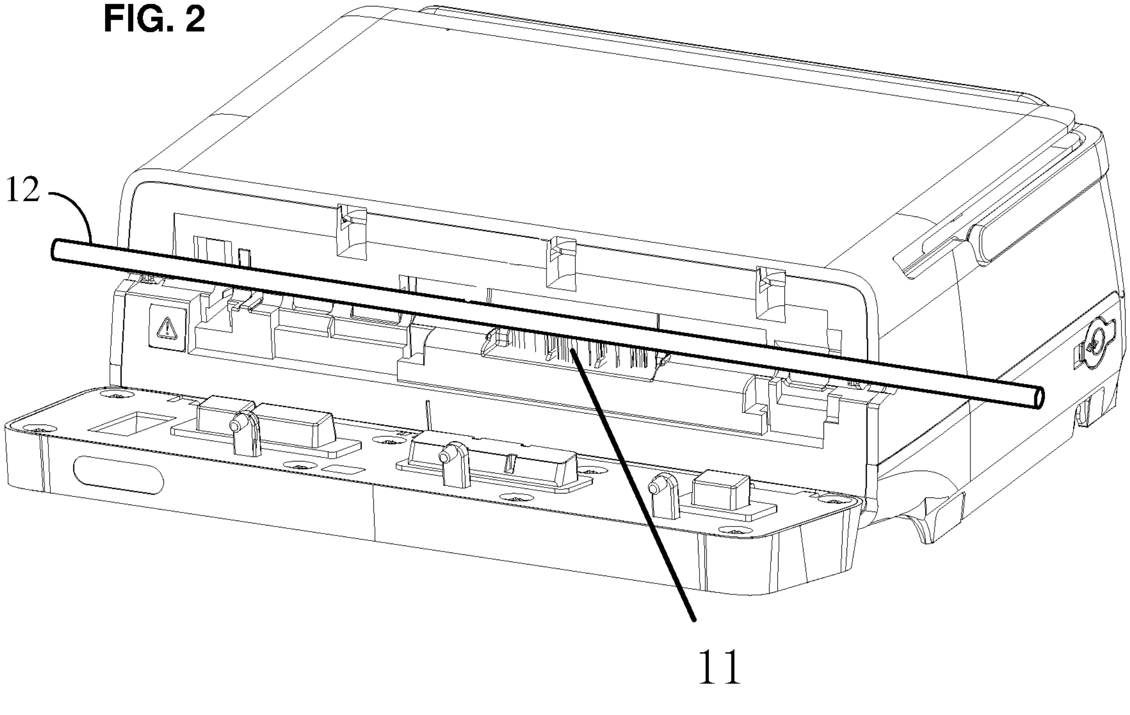
FIG. 2 shows a schematic diagram of an infusion pump according to an embodiment of the invention.

FIG. 1 is a flowchart of a control method of an infusion pump according to an embodiment of the invention, which can be applied to the infusion pump of FIG. 2. As shown in FIG. 2, the infusion pump includes a controller (not specifically shown in the figure), a drive mechanism (not specifically shown in the figure), an extrusion member 11, and an infusion consumable 12. The drive mechanism is connected to the extrusion member 11 in a transmission way. The infusion consumable 12 is a tube configured to deliver a fluid, one end of which is connected to the fluid storage device and the other end of which is used to connect to the patient. The infusion consumable 12 is disposed in the infusion pump, and the extrusion member 11 is disposed on the wall of the tube of the infusion consumable 12. During operation of the infusion pump, the controller controls the drive mechanism to operate, thereby driving the extrusion member 11 to apply pressure to the infusion consumable 12, and further driving the fluid flow in the infusion consumable 12. As shown in FIG. 1, the method specifically includes the following steps.

S10, identification information and/or consumable information of a target infusion consumable set to the infusion pump is determined.

Specifically, the infusion pump shown in FIG. 2 further includes a consumable identification device and/or an interaction device (neither of which is shown in the figures) in communication with the controller of the infusion pump. By means of the identification device or the interaction device, the identification information and/or the consumable information of the target infusion consumable currently set to the infusion pump can be determined.

The infusion consumable 12 generally refers to a tube configured to deliver the fluid. The identification information may include one or more of a brand, a model, a serial number, a code, etc., of the infusion consumable. The consumable information may include one or more of material information of the infusion consumable, tube wall thickness information, inner and outer diameter information of the tube, and tube pre-pressurization volume information.

In some embodiments of the invention, the infusion consumable 12 is provided with an identification portion (not shown in the figures) for identification by the consumable identification device, and different brands or types of infusion consumables 12 may be provided with different identification portions.

For example, the identification portion may be a coating provided on the tube body of the infusion consumable 12, which may be formed by coating with materials such as ink, pigment, etc. The identification portion may also be a specific identification pattern in the form of dots or other shapes, which may be formed by ink, pigment, etc., or by pasting, engraving, etc. The identification portion may also be a label such as a two-dimensional code, barcode, or the like. Accordingly, the consumable identification device may be of various types according to the different types of identification sections, for example, the consumable identification device may be an image sensor, a contact sensor, a reflective light sensor, a contra-reflective light sensor, a decoder, and the like.

The infusion pump is provided with a consumable mounting position. When the target infusion consumable is placed on the consumable mounting position, the identification portion of the target infusion consumable positioned relative to the consumable identification device of the infusion pump so that the consumable identification device can detect the identification portion and identify the brand or type of the target infusion consumable, so as to determine the identification information and/or the consumable information of the target infusion consumable. Upon completion, the consumable identification device feeds the identification results back to the controller of the infusion pump.

In some embodiments of the invention, the identification information and/or consumable information of the target infusion consumable set to the infusion pump may also be determined by the interaction device.

The interaction device may be, for example, a touch screen, a keypad, or a third-party electronic device provided on the infusion pump that is in communication with the infusion pump. For example, the infusion pump may be provided with a display screen having a touch control function, and when a consumable parameter input start operation is detected, a parameter input interface is displayed on the display screen of the infusion pump according to the start operation. The user may input the identification information and/or consumable information of the target infusion consumable through the parameter input interface. The consumable parameter input start operation may, but is not limited to, be a start operation for a specific key set in advance on the infusion pump.

It should be noted that in some embodiments of the invention, if the infusion consumable does not have an identification portion, the user may not know the specific information of the infusion consumable, that is to say, it may not be possible to determine the identification information and/or the consumable information of the target infusion consumable set to the infusion pump. In such a case, the user may select the identification information and/or the consumable information of the infusion consumable that is approximate to this target infusion consumable as the identification information and/or the consumable information of the target infusion consumable via the interaction device.

S20, a control rule of the infusion pump corresponding to the target infusion consumable is determined according to the identification information and/or the consumable information.

Specifically, the infusion pump includes a storage unit configured to store identification information, consumable information, and control rules corresponding to the respective identification information and/or the respective consumable information for each of the infusion consumables. The controller of the infusion pump may, according to the acquired identification information and/or the consumable information, determine the control rules pre-stored in the infusion pump corresponding to the target infusion consumable.

The control rule indicates a relationship between various operating parameters of the infusion pump, and the operating parameters may include, but are not limited to, one or more of: a motor speed of the infusion pump, a pressure of the infusion pump, a voltage of the infusion pump, a current of the motor of the infusion pump, an infusion speed of the infusion pump, and the like. The various operating parameters of the infusion pump may be obtained by various sensors, detection components, and the like mounted on the infusion pump. For example, the motor speed may be detected by a rotational speed sensor, the pressure of the infusion pump may be detected by a pressure sensor, the voltage of the infusion pump may be detected by a voltage sensor, the current of the infusion pump may detected by a current sensor, and the infusion speed may be detected by a flow rate sensor, etc.

Specifically, the control rules may include, but are not limited to, at least one of: an infusion accuracy control rule, an obstruction pressure control rule, a bubble judgment rule, and a drive mechanism current adjustment rule. The infusion accuracy control rule indicates a relationship between the infusion pump motor speed and the infusion speed, and different infusion pump motor speeds correspond to different infusion speeds, and the infusion speed of the infusion pump may be changed by adjusting the infusion pump motor speed. The blocking pressure control rule indicates a relationship between the blocking pressure and voltage of the infusion pump. Different blocking pressures correspond to different voltage values, and an alarm may be issued when the voltage value reaches a preset alarm threshold. The bubble judgment rule indicates a relationship between the infusion pump voltage and bubble volume size. Different volume sizes of bubbles correspond to different voltage values, and the bubble volume size may be determined by calculating the product of the time to reach the bubble threshold and the infusion speed. The drive mechanism current adjustment rule indicates a relationship between the motor current of the infusion pump and different infusion consumables. Due to the differences in the material and mechanical properties of different infusion consumables, different infusion consumables correspond to different motor currents, and the accurate control of the motor current corresponding to each infusion consumable can extend the duration and reduce the operating temperature to achieve the purpose of saving energy.

It is to be noted that there will in most cases be a plurality of control rules corresponding to the infusion consumables pre-stored in the infusion pump, different types of infusion consumables may correspond to different control rules, and each type of infusion consumable may correspond to a plurality of control rules.

Further, since different kinds of infusion consumables are made of different materials and have different inner diameters, outer diameters, tube wall thicknesses, tube preload amounts, and other parameters, each infusion consumable corresponds to a different resistance and resilience, and accordingly, different kinds of infusion consumables correspond to different control rules. That is, different kinds of infusion consumables correspond to different operating parameters. For infusion consumables made of harder materials, their corresponding motor speed and motor current are larger in order to reduce the resistance and ensure the normal operation of the infusion pump. For example, with the same inner and outer diameter, but different hardness of two infusion consumables—consumable A and consumable B—, the tube hardness of the infusion consumable A might be 60 HB, such that the infusion pump motor speed might need to be 1 r/s to obtain 100 ml/h infusion speed; whereas the tube hardness of the infusion consumable B might be 70 HB and require an infusion pump motor speed of 1.05 r/s to obtain a 100 ml/h infusion speed.

The control rules indicate one or more of the control logic, the operating parameters, and the relationship between the operating parameters of the infusion pump; the infusion pump thereby performs the corresponding operation according to each of the operating parameters in the control rules during operation. The controller of the infusion pump may select the control rule corresponding to the target infusion consumable according to the obtained identification information and/or consumable information of the target infusion consumable, and cause the infusion pump to operate according to each of the operation parameters indicated by the control rule, so as to make the operation of the infusion pump more convenient and more accurate.

S30, the control rule corresponding to the target infusion consumable is adjusted according to the preset correction rule.

The preset correction rules corresponding to the identification information and/or consumable information of each infusion consumable are also stored in the storage unit of the infusion pump. When the identification information and/or the consumable information of the target infusion consumable set to the infusion pump is determined, the controller of the infusion pump can match the preset correction rules stored within the infusion pump corresponding to the target infusion consumable, and the control rules corresponding to the target infusion consumable, according to the identification information and/or the consumable information of the target infusion consumable. The controller of the infusion pump then adjusts the control rule of the target infusion consumable according to that preset correction rule.

The preset correction rule indicates a relationship between the correction parameters and the control rule, and the relationship between the correction parameters and the control rule may be confirmed according to a preset mapping relationship, a functional relationship, self-learning, or the like. The correction parameters may be preset or may be calculated according to the feedback information from the infusion pump during a preset time period.

As an example, if the control rule of the target infusion consumable is F1(x), the control rule of the target infusion consumable may be adjusted to F2(x) according to the relationship between the correction parameter and the control rule and the preset correction rule. $F2(x)=k\cdot F1(x)$, where x denotes the motor speed of the infusion pump, F1(x), F2(x) denotes the infusion speed, and k denotes the correction parameter.

In some embodiments of the invention, the step S30 of adjusting the control rule corresponding to the target infusion consumable according to the preset correction rule may include the following sub-step:

adjusting the control rule of the target infusion consumable according to the relationship between the correction parameter and the control rule according to the preset correction parameter.

It is to be noted that the target infusion consumable may include a plurality of control rules, such as an infusion accuracy control rule F1(x), a blocking pressure control rule G1(x), a bubble judgment rule H1(x), and a drive mechanism current adjustment rule I1(x), and the correction parameters corresponding to each of the control rules may be the same or different. For example, the adjusted infusion accuracy control rule might be $F2(x)=F1(x)+k1$, and the adjusted blocking pressure control rule might be $G2(x)=G1(x)+k2$; where k1, k2 denote different correction parameters, respectively.

Since the correction parameters may be preset, when the identification information and/or the consumable information of the target infusion consumable set to the infusion pump is determined, the controller of the infusion pump may directly and automatically adjust the control rule of the target infusion consumable according to the preset correction parameters and the relationship between the correction parameters and the control rule, so as to make the calibration method of the infusion pump more convenient and more accurate.

In some embodiments of the invention, the step S30 of adjusting the control rule corresponding to the target infusion consumable according to the preset correction rule, may further include the following sub-steps:

S31: the infusion pump is operated according to the control rule corresponding to the target infusion consumable.

Specifically, the control rule in this example may indicate one or more of a control logic of the infusion pump, an operating parameter, and a relationship among the operating parameters, and each operating parameter in the control rule of the target infusion consumable may be determined so that the infusion pump performs a corresponding operation according to the operating parameter. For example, the infusion pump is caused to operate according to the motor speed of the infusion pump in the control rule.

S32, feedback information of the infusion pump during a preset time period is obtained. The feedback information includes fluid information of the infusion pump.

Specifically, in the step of obtaining the feedback information of the infusion pump during the preset time period, a data acquisition device in communication with the infusion pump is configured to obtain the liquid information of the infusion pump, and the data acquisition device may transmit the collected liquid information as feedback information to the controller of the infusion pump.

As an example, the data acquisition device may include an electronic weighing device or a pressure sensor. The electronic weighing device may capture a weight of the liquid output from the infusion pump and use the captured weight of the liquid as a form of feedback information. In addition, when the data collection device is a pressure sensor, the pressure sensor may collect a liquid pressure value of the liquid output from the infusion pump to use the liquid pressure value as a kind of feedback information.

S33, a preset correction rule is determined according to the feedback information, and the control rule of the target infusion consumable is adjusted according to the preset correction rule.

Specifically, the liquid flow rate may be calculated according to the time corresponding to the weight of the liquid collected by the electronic weighing device; alternatively, the liquid flow rate may be calculated by the liquid pressure value collected by the pressure sensor. Thereafter, the calculated liquid flow rate is compared with the liquid flow rate in the control rule, and the correction parameter is determined. The controller of the infusion pump makes adjustments to the target control rule of the infusion consumable is adjusted.

The correction parameter may be determined according to a difference, a ratio, or other preset functional relationship between the calculated liquid flow rate and the liquid flow rate in the control rule.

It is to be noted that the target infusion consumable may include a plurality of control rules, such as the infusion accuracy control rule F(x), the blocking pressure control rule G(x), the bubble judgment rule H(x), the drive mechanism current adjustment rule I(x), etc., and step 33 may further include the following sub-steps.

S331, a preset correction rule corresponding to the first control rule of the target infusion consumable is determined according to the feedback information;

S332, at least one control rule of the target infusion consumable is adjusted according to the preset correction rule of the first control rule.

As an example, if the first control rule is the infusion accuracy control rule F(x), the liquid flow rate may be calculated according to the time corresponding to the weight of the liquid captured by the electronic weighing device. Thereafter, the calculated liquid flow rate is compared with the liquid flow rate in the infusion accuracy control rule F(x), and a correction parameter k is determined. According to the preset correction rule, i.e., the relationship between the correction parameter k and the infusion accuracy control rule F(x), the infusion accuracy control rule F(x) is adjusted. Meanwhile, other control rules, such as the blocking pressure control rule G(x), the bubble judgment rule H(x), and the drive mechanism current adjustment rule I(x), may be adjusted respectively according to the correction parameter k determined by the infusion accuracy control rule F(x).

In the invention, a preset correction rule is determined according to the feedback information of the operation of the infusion pump during a preset time period, and the control rule of the target infusion consumable is adjusted according to the preset correction rule, which can make the calibration method of the infusion pump more accurate.

Further, in some embodiments of the invention, after step S33, it may further include: adjusting the respective control rules of other kinds of infusion consumables stored in the infusion pump according to the preset correction rule.

If the above approach is adopted, the controller of the infusion pump determines a preset correction rule corresponding to the target infusion consumable according to the feedback information of the operation of the infusion pump during the preset time period, and may also adjust the control rules of the other kinds of infusion consumables stored within the infusion pump according to the preset correction rule, so as to make the calibration method of the infusion pump more accurate.

Further, in some embodiments of the invention, after step S33, it may further include: determining actual consumable information of the target infusion consumable set on the infusion pump according to the feedback information.

The actual consumable information may include one or more of: material information of the infusion consumable, tube wall thickness information, tube inner and outer diameter information, and tube preload amount information.

As an example, if the blocking pressure control rule is $G(x)=a\cdot b^{c\cdot x}+d$, in which a denotes the material information, b denotes the tube wall thickness information, c denotes the tube inner and outer diameter information, d denotes the tube preload amount information, x denotes the voltage value, and G(x) denotes the blocking pressure value. The unit of G(x) is Newtons (N). The parameter a represents such physical properties of the material as the modulus of elasticity, which can be converted to a force value, since the force area is constant for the pressure sensor). The parameters b and c may be represented as dimensionless physical quantities. The variable x varies with time. The parameter d is the value of the force (unit: N) in the initial state when the infusion tube is compressed. The formula thus refers to the stress relaxation theory in the mechanics of materials. By taking the 4 sets of test results (G(x1), x1), (G(x2), x2), (G(x3), x3), (G(x4), x4) into $G(x)=a\cdot b^{c\cdot x}+d$, the values of a, b, c, and d can be computed, thus the actual consumable information of the target infusion consumable is determined.

The infusion pump may store identification information for a plurality of infusion pumps and preset consumable information corresponding to each. If the determined actual consumable information deviates from the preset consumable information stored within the infusion pump, the controller of the infusion pump may update the preset consumable information stored within the infusion pump, i.e., replace the original preset consumable information with the actual consumable information, thereby calibrating the preset consumable information stored within the infusion pump.

Further, the controller of the infusion pump may also compare the actual consumable information with the preset consumable information of the target infusion consumable, and if the deviation value between the actual consumable information and the preset consumable information is large, it indicates that the user may place an incorrect infusion consumable on the infusion pump, and the system will send out an alarm prompt at this time.

For example, when calibrating the infusion consumable A, if the user mistakenly places the infusion consumable B on the infusion pump, the calculated actual consumable information of the infusion consumable B will have a large deviation value from the preset consumable information of the infusion consumable A. The system may then issue an alarm prompting the incorrect selection of the infusion consumable.

In some embodiments of the invention, the step S30 is included, and involves adjusting the control rule corresponding to the target infusion consumable according to the preset correction rule, which may further include the following sub-steps.

S301, a preset initial compensation parameter $m_0$ and a preset step size n within the infusion pump are obtained.

S302, a deviation value of a product $m_0 \cdot G(x)$ of the initial compensation parameter $m_0$ and the control rule of the target infusion consumable G(x) from the control rule of the target infusion consumable G(x) are calculated, where G(x) is the liquid flow rate.

S303, if the deviation value does not satisfy a preset deviation threshold, the initial compensation parameter $m_0$ is adjusted according to a preset step size n to obtain the adjusted compensation parameter $m_1$, in which $m_1=m_0+n$.

A deviation value of a product $m_1 \cdot G(x)$ of the adjusted compensation parameter $m_1$ and the control rule of the target infusion consumable G(x) from the control rule of the target infusion consumable G(x) are calculated.

S304, if the deviation value satisfies the preset deviation threshold, the adjusted compensation parameter $m_1$ is determined as a correction parameter, and then the control rule of the target infusion consumable is adjusted according to the preset correction rule, i.e., the relationship between the correction parameter and the control rule.

S305, if the deviation value still does not satisfy the preset deviation threshold, the step S303 is repeated. The compensation parameter $m_1$ is adjusted according to the preset step size n to obtain the adjusted compensation parameter $m_2$, in which $m_2=m_1+n$. A deviation value of a product $m_2 \cdot G(x)$ of the adjusted compensation parameter $m_2$ and the control rule of the target infused consumable G(x) and the control rule of the target infused consumable G(x) are determined, and whether the deviation value satisfies the deviation threshold is determined. If so, the compensation parameter $m_n$ after this adjustment is determined as a correction parameter according to step S304, and then the control rule of the target infusion consumable is adjusted according to the preset correction rule, i.e., the relationship between the correction parameter and the control rule. If not, the step S303 is repeated until the deviation value satisfies the preset deviation threshold.

It is to be noted that the target infusion consumable may include a plurality of control rules, such as the infusion accuracy control rule F(x), the blocking pressure control rule G(x), the bubble judgment rule H(x), the drive mechanism current adjustment rule I(x), and the like. If a correction parameter of the blocking pressure control rule G(x) is determined to be $m_n$ according to the above-described manner, other control rules of the target infusion consumable may be adjusted, such as the infusion accuracy control rule F(x), the bubble judgment rule H(x), and the drive mechanism current adjustment rule I(x) are adjusted according to the correction parameter $m_n$.

If the above approach is adopted, the controller of the infusion pump determines a preset correction rule corresponding to the target infusion consumable according to the compensation parameter, and may also adjust the control rules of other kinds of infusion consumables stored in the infusion pump according to the determined preset correction rule, so as to make the calibration method of the infusion pump more accurate.

Further, in some embodiments of the invention, the above-described control method of the infusion pump further includes operating the infusion pump according to the adjusted control rules.

After completing this calibration, operating the infusion pump according to the adjusted control rule may improve the accuracy of the monitoring.

Further, in some embodiments of the invention, the above-described control method of the infusion pump further includes updating the control rule of the target infusion consumable.

When the infusion pump completes the current infusion, the control rule corresponding to the target infusion consumable pre-stored in the infusion pump may be updated to the adjusted control rule, so that if the infusion consumable of the same type is mounted to the infusion pump next time, it can be operated according to the updated control rule, which can improve the accuracy of the monitoring.

Further, in some embodiments of the invention, the above control method of the infusion pump further includes outputting the updated control rule of the target infusion consumable.

After the infusion pump completes the infusion, it updates the control rules of the target infusion consumable, and may send the updated control rules of the target infusion consumable to an external device connected to the infusion pump. The external device may include an infusion workstation, a remote terminal, or other infusion pumps, and the like. Each infusion pump may then send the updated control rules of the target infusion consumable to the external device, which allows data interaction among different infusion pumps. When the same type of infusion consumable is mounted to other infusion pumps, it can be operated directly according to the updated control rules, so as to improve the accuracy of monitoring.

Figure 3:
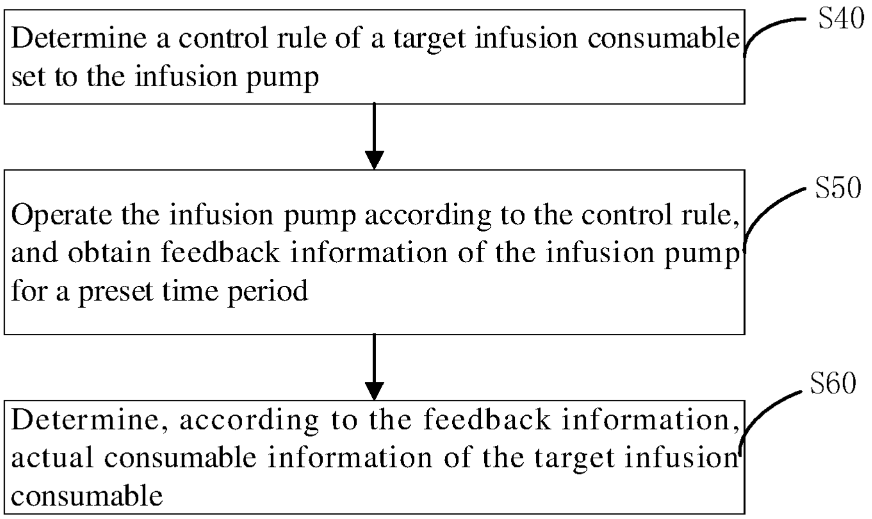
FIG. 3 shows a flowchart of the control method of the infusion pump according to another embodiment of the invention.

FIG. 3 shows a flowchart of the control method of the infusion pump according to another embodiment of the invention. As shown in FIG. 3, the method specifically includes the following steps.

S40, a control rule of a target infusion consumable set to the infusion pump is determined.

In some embodiments of the invention, if the identification information and/or the consumable information of the target infusion consumable set to the infusion pump is known, that is to say, the identification information and/or the consumable information of the target infusion consumable, which may be obtained by a consumable identification device and/or an interaction device in communication with with the controller of the infusion pump. Therefore, the controller of the infusion pump may determine the control rule of the infusion pump corresponding to the target infusion consumable according to the acquired identification information and/or consumable information.

Specifically, step S40 may include the following sub-steps.

S41, the identification information and/or consumable information of the target infusion consumable set to the infusion pump is determined. Since step S41 is the same as step S10 of the preceding embodiment, the specific realization thereof is not described herein.

S42, a control rule corresponding to the target infusion consumable of the infusion pump is determined according to the identification information and/or the consumable information. Since step S42 is the same as step S20 of the preceding embodiment, the specific realization thereof is not repeated herein.

In some embodiments of the invention, the controller of the infusion pump may be unable to acquire the identification information and/or the consumable information of the target infusion consumable set to the infusion pump, that is to say, the specific information of the target infusion consumable cannot be recognized by the consumable identification device in communication with the controller of the infusion pump. In this circumstance, the user may select, by the interaction device, the identification information and/or the consumable information approximating the target infusion consumable, and use the control rule stored in the infusion pump corresponding to the identification information and/or the consumable information approximating the target infusion consumable as the control rule corresponding to the target infusion consumable.

S50, the infusion pump is operated according to the control rule corresponding to the target infusion consumable, and feedback information of the infusion pump for a preset time period is obtained. The feedback information includes fluid information of the infusion pump;

Specifically, the control rule indicates a relationship between various operating parameters of the infusion pump, and various operating parameters in the control rule of the target infusion consumable may be determined such that the infusion pump performs a corresponding operation to operate the infusion pump according to the operating parameters. For example, the infusion pump is operated according to a motor speed of the infusion pump in the control rule.

In the step of obtaining feedback information of the infusion pump during the preset time period, a data acquisition device in communication with the infusion pump is configured to obtain liquid information of the infusion pump, and transmit the collected liquid information as feedback information to the controller of the infusion pump.

As an example, the data collection device may include an electronic weighing device or a pressure sensor. The electronic weighing device may capture the weight of the liquid output from the infusion pump and use the captured weight of the liquid as a form of feedback information. In addition, when the data acquisition device is a pressure sensor, the pressure sensor may capture a liquid pressure value of the liquid output from the infusion pump, and use the liquid pressure value as a form of feedback information.

S60, actual consumable information of the target infusion consumable is determined according to the feedback information.

The actual consumable information may include one or more of: material information of the infusion consumable, tube wall thickness information, tube inner and outer diameter information, and tube pre-pressure volume information.

As an example, if the blocking pressure control rule is $G(x)=a\cdot b^{c\cdot x}+d$, in which a denotes the material information, b denotes the tube wall thickness information, c denotes the tube inner and outer diameter information, d denotes the tube preload amount information, x denotes the voltage value, and G(x) denotes the blocking pressure value. By taking the 4 sets of test results (G(x1), x1), (G(x2), x2), (G(x3), x3), (G(x4), x4) into $G(x)=a\cdot b^{c\cdot x}+d$, the values of a, b, c, and d can be computed, thus the actual consumable information of the target infusion consumable is determined.

In some embodiments of the invention, the above-described control method of the infusion pump further includes comparing the actual consumable information with a plurality of sets of preset consumable information stored within the infusion pump, and determining the identification information of the target infusion consumable.

Specifically, there may be a plurality of sets of identification information of the infusion pump stored in the infusion pump, and preset consumable information corresponding to each identification information. If the target infusion consumable set on the output pump is an unknown brand of infusion consumable, the controller of the infusion pump may then compare the calculated actual consumable information with the plurality of sets of preset consumable information stored in the infusion pump, and the identification information of the target infusion consumable can be determined, so as to realize the unknown brand of infusion consumables identification.

Further, in some embodiments of the invention, the above control method of the infusion pump further includes outputting the identification information of the target infusion consumable.

Specifically, the controller of the infusion pump may control a display device of the infusion pump to display the identification information of the target infusion consumable, or may send the identification information of the target infusion consumable to an external device connected to the infusion pump, so as to facilitate the user to understand the specific information of the target infusion consumable.

Further, in some embodiments of the invention, the above control method of the infusion pump further includes the following steps.

S71, the identification information of the target infusion consumable is obtained.

S72, the preset consumable information associated with the identification information is determined according to the identification information.

S73, a deviation value between the actual consumable information and the preset consumable information is calculated, and an alarm prompt is issued when the deviation value reaches a preset deviation threshold.

Specifically, if the identification information of a target infusion consumable set to the infusion pump is known, the controller of the infusion pump may obtain the identification information of the target infusion consumable by a consumable identification device and/or an interaction device in communication with the controller of the infusion pump, and match the preset consumable information corresponding to the identification information within the infusion pump. If the deviation value between the actual consumable information and the preset consumable information reaches a preset deviation threshold, it indicates that the user may have placed the wrong infusion consumable on the infusion pump, or the user has selected the wrong identification information. In this circumstance, the system will issue an alarm prompt.

For example, when calibrating the infusion consumable A, if the user mistakenly places the infusion consumable B on the infusion pump, the calculated actual consumable information of the infusion consumable B will have a large deviation value from the preset consumable information of the infusion consumable A. In this circumstance, the system may issue an alarm prompting the incorrect selection of the infusion consumable.

Further, if the determined actual consumable information deviates from the preset consumable information stored in the infusion pump, the preset consumable information stored in the infusion pump may be updated, i.e., the actual consumable information is used to replace the original preset consumable information, so as to calibrate the preset consumable information stored in the infusion pump.

In some embodiments of the invention, the above control method of the infusion pump further includes adjusting the control rule stored within the infusion pump associated with the actual consumable information.

Specifically, the control rules stored within the infusion pump associated with the actual consumable information may be adjusted according to the preset correction rules. Since the manner of adjusting the control rules according to the preset correction rules is the same as that of step S30 of the preceding embodiment, the specific realization thereof will not be repeated herein.

FIG. 2 shows an infusion pump according to another embodiment of the invention. The infusion pump includes a controller (not specifically shown in the figures), a drive mechanism (not specifically shown in the figures), an extrusion member 11, and an infusion consumable 12. The drive mechanism is connected to the extrusion member 11 by means of a transmission. The infusion consumable 12 is a tube configured to convey fluid, one end of which is connected to a fluid storage device, and the other end of which is configured to be connected to a patient. The infusion consumable 12 is arranged through the infusion pump, and the extrusion member 11 is provided on a tube wall of the infusion consumable 12. During operation of the infusion pump, the controller controls the drive mechanism to operate, to drive the extrusion member 11 to apply pressure to the infusion consumable 12, thereby driving the fluid flow in the infusion consumable 12.

Specifically, the controller causes the infusion pump to perform the following control method:

- determining identification information and/or consumable information of a target infusion consumable set to the infusion pump;
- determining, according to the identification information and/or consumable information, a control rule corresponding to the target infusion consumable of the infusion pump;
- adjusting the control rule corresponding to the target infusion consumable according to a preset correction rule.

In an embodiment, determining the identification information and/or the consumable information of the target infusion consumable set to the infusion pump includes determining the identification information and/or consumable information of the target infusion consumable by a consumable identification device and/or an interaction device in communication with the infusion pump.

In an embodiment, the step of adjusting the control rule corresponding to the target infusion consumable according to the preset correction rule, includes:

- operating the infusion pump according to the control rule corresponding to the target infusion consumable;
- obtaining feedback information of the infusion pump for a preset time period; wherein the feedback information comprises fluid information of the infusion pump; and
- determining, according to the feedback information, the preset correction rule, and adjusting the control rule of the target infusion consumable according to the preset correction rule.

In an embodiment, the target infusion consumable includes a plurality of control rules;

- the step of determining, according to the feedback information, the preset correction rule and adjusting the control rule of the target infusion consumable according to the preset correction rule, comprises:
- determining, according to the feedback information, a preset correction rule corresponding to a first control rule of the target infusion consumable; and
- adjusting at least one control rule of the target infusion consumable according to the preset correction rule of the first control rule.

In an embodiment, the infusion pump has a plurality of control rules for a plurality of infusion consumables stored therein; the method further includes: adjusting a control rule of at least one other type of infusion consumable stored within the infusion pump according to the preset correction rule.

In an embodiment, the method further includes updating the control rules of the target infusion consumable.

Figure 4:
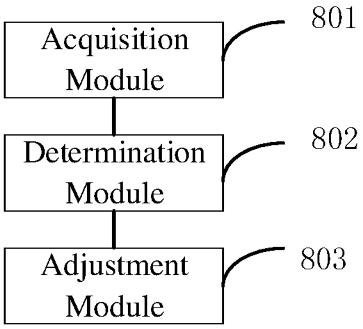
FIG. 4 shows a structural schematic diagram of a control device of the infusion pump according to an embodiment of the invention.

FIG. 4 shows a structural schematic diagram of a control device of an infusion pump according to another embodiment of the invention, in which the device includes an acquisition module 801, a determination module 802, and an adjustment module 803.

The acquisition module 801 is configured to determine identification information and/or consumable information of a target infusion consumable set to the infusion pump.

The determination module 802 is configured to determine a control rule of the infusion pump corresponding to the target infusion consumable according to the identification information and/or the consumable information.

The adjustment module 803 is configured to adjust the control rule corresponding to the target infusion consumable according to the preset correction rule.

In an embodiment, the control rule may include, but is not limited to, at least one of: an infusion accuracy control rule, a blocking pressure control rule, a bubble judgment rule, and a drive mechanism current adjustment rule.

In an embodiment, the acquisition module 801 is configured to determine identification information and/or consumable information of the target infusion consumable according to the consumable identification device and/or the interaction device in communication with the infusion pump.

In an embodiment, the adjustment module 803 may include:

- an operating unit configured to operate the infusion pump according to a control rule corresponding to the target infusion consumable;
- an acquisition unit configured to acquire feedback information of the infusion pump during a preset time period, the feedback information including fluid information of the infusion pump; and
- an analyzing unit configured to determine a preset correction rule according to the feedback information and adjust the control rule of the target infusion consumable according to the preset correction rule.

In an embodiment, the target infusion consumable includes a plurality of control rules, and the analyzing unit may include:

- a correction rule confirmation unit configured to determine, according to feedback information, a preset correction rule corresponding to the first control rule of the target infusion consumable; and
- an adjustment unit configured to adjust each control rule of the target infusion consumable according to the preset correction rule of the first control rule.

In an embodiment, the infusion pump stores control rules of a plurality of infusion consumables, and the adjustment module 803 may include a regulating unit configured to regulate the respective control rules of other kinds of infusion consumables stored within the infusion pump according to the preset correction rules.

In an embodiment, the adjustment module 803 further includes:

a consumable determination unit configured to determine actual consumable information of the target infusion consumable according to the feedback information.

In an embodiment, the device further includes an update module configured to update the control rules of the target infusion consumable.

Figure 5:
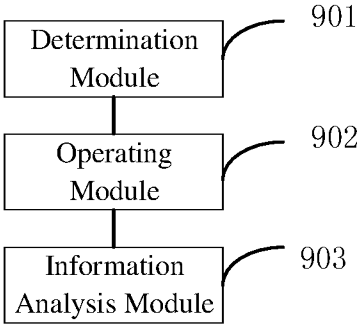
FIG. 5 shows a structural schematic diagram of the control device of the infusion pump according to another embodiment of the invention.

FIG. 5 shows a structural schematic diagram of a control device of an infusion pump according to another embodiment of the invention, in which the device includes a determination module 901, an operating module 902, and an information analysis module 903.

The determination module 901 is configured to determine a control rule of a target infusion consumable set to the infusion pump.

The operating module 902 is configured to operate the infusion pump according to the control rule and obtain feedback information of the infusion pump during a preset time period, the feedback information including liquid information of the infusion pump.

The information analysis module 903 is configured to determine the actual consumable information of the target infusion consumable based on the feedback information.

In an embodiment, the control rules may include, but are not limited to, at least one of: an infusion precision control rule, a blocking pressure control rule, a bubble judgment rule, and a drive mechanism current adjustment rule.

In an embodiment, the infusion pump stores a preset information for a plurality of consumables, and identification information of the infusion supplied associated with each preset consumable information. The device further includes an identification module configured to compare the actual consumable information with the plurality of preset consumable information stored within the infusion pump to determine the identification information of the target infusion consumable.

In an embodiment, the device further includes an output module configured to output the identification information of the target infusion consumable.

In an embodiment, the infusion pump stores the identification information of a plurality of infusion consumables, as well as the preset consumable information associated with each identification information. The device further includes:

an identification acquisition module configured to acquire the identification information of the target infusion consumables;

a preset information acquisition module configured to determine, according to the identification information, preset consumable information associated with the identification information; and an alarm module configured to calculate a deviation value between the actual consumable information and the preset consumable information, and issue an alarm prompt when the deviation value reaches a preset deviation threshold.

In an embodiment, the device further includes an adjustment module configured to adjust the control rules stored in the infusion pump associated with the actual consumable information.

In other embodiments, in response to the above technical problems in the prior art, the invention proposes a calibration method and a device of an infusion pump, an electronic device and readable medium, in which the property parameters of the infusion tube connected to the infusion pump are obtained, and a preset control function used to calibrate the infusion pump is determined according to the property parameters. An adjustment coefficient of the infusion pump is determined according to the preset control function, and then the preset control function of the infusion pump is adjusted according to the adjustment coefficient. The method of the invention achieves more accurate calibration of the infusion pump by adjusting the preset control function according to determined adjustment coefficients.

The technical solutions of the invention and how the technical solutions of the invention solve the above technical problems are described in detail below by means of specific embodiments. These following specific embodiments may be combined with each other, and the same or similar concepts or processes may not be repeated in certain embodiments. Embodiments of the invention will be described below in conjunction with the accompanying drawings.

Figure 6:
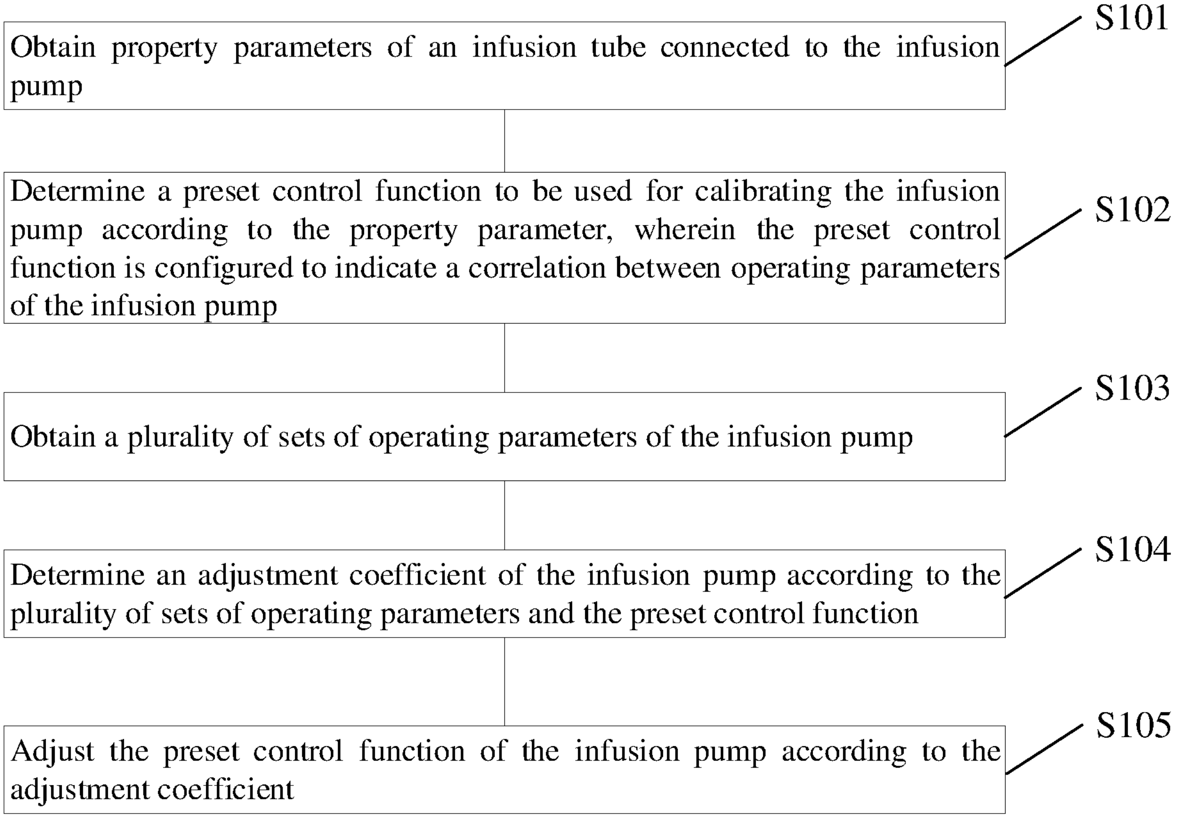
FIG. 6 shows a flowchart of a calibration method of an infusion pump according to an embodiments of the invention.

FIG. 6 shows a flowchart of a calibration method of an infusion pump according to an embodiment of the invention. An execution subject of the method may be a device or an electronic device having a calibration function of the infusion pump, for example, it may be a server, a personal computer, a laptop computer, a smartphone, a tablet computer, or a portable wearable device, and the like. The method in this embodiment may be implemented by means of software, hardware, or a combination of hardware and software. As shown in FIG. 6, the method specifically includes the following steps.

S101, property parameters of an infusion tube connected to the infusion pump are obtained.

The infusion pump needs to be used together with the infusion tube, and the liquid in an infusion bottle or bag flows into the infusion pump through the infusion tube. There are many types of infusion tubes, and different types correspond to different property parameters, the property parameters include, but are not limited to: infusion tube material information, tube wall thickness information, tube inner and outer diameter information and tube preload amount information

S102, a preset control function used to calibrate the infusion pump is determined according to the property parameters. The preset control function is used to indicate the correlation between the operating parameters of the infusion pump.

The preset control function is preset in the infusion pump, and the preset control function is associated with the type of the infusion tube connected to the infusion pump, i.e., if the type of the infusion tube connected to the infusion pump is different, the preset control function is also different.

Therefore, according to the obtained property parameters of the infusion tube connected to the infusion pump, the preset control function used for calibrating the infusion pump can be determined.

In the invention, the preset control function may be one or more of the following: a preset control function between a motor speed of the infusion pump and the speed of infusion, a preset control function between an occlusion pressure and a voltage of the infusion pump, a preset control function between the voltage of the infusion pump and a bubble volume size of the infusion tube, and a preset control function between an infusion pump occlusion pressure and a motor current.

It can be understood that the preset control function may also include a control function between other infusion pump operating parameters, which is not limited herein in the invention.

S103, a plurality of sets of operating parameters of the infusion pump are obtained.

In the invention, the operating parameters may include, but are not limited to: the motor speed of the infusion pump, the infusion pump occlusion pressure, the infusion pump voltage, the motor current of the infusion pump, and the infusion rate of the infusion pump.

One possible implementation is as follows.

Various operating parameters of the infusion pump are measured by various sensors and measurement components arranged on the infusion pump, such as the motor speed is measured by a rotation speed sensor. The infusion pump occlusion pressure is measured by a pressure sensor. The infusion pump voltage is measured by a voltage sensor. The infusion pump current is measured by a current sensor. The infusion rate is measured by a flow rate sensor.

The infusion rate may be obtained in at least the following two ways, in addition to being obtained by the direct measurement.

One way is as follows: The liquid volume in the infusion tube connected to the infusion pump is measured, which is assumed to be V1. A duration of time that the liquid flows in and out of the infusion tube is measured, which is assumed to be T1. The liquid volume V1 is divided with the duration of time T1, i.e., V1/T1, so as to obtain the infusion rate.

The other way is as follows. The liquid mass that flows out in a duration of time T2 is measured, and the liquid volume can be calculated according to the known density of the liquid, which is assumed to be V2. The liquid volume V2 is divided with the duration of time T2 i.e., V2/T2, so as to obtain the infusion rate.

S104, an adjustment coefficient of the infusion pump is determined according to a plurality of sets of operating parameters and the preset control function.

S105, the preset control function of the infusion pump is adjusted according to the adjustment coefficient.

In this example, it may be assumed that the preset control function used to calibrate the infusion pump is linear, that is, in the form F1(x)=a*x+b. where x indicates the motor speed of the infusion pump, a and b are coefficients that may be determined through testing of the respective configuration, and F1(x) indicates the infusion rate According to the obtained operating parameters, namely the motor speed of the infusion pump and the infusion rate, the above preset control function F1(x)=a*x+b is adjusted, so as to obtain the adjusted control function F1(x)=a1*x+b1 between the motor speed and the infusion speed.

It can be understood that the preset control function may also have different forms, which may be set according to the user's fitting method between different operating parameters. For example, it may also be F1(x)=a*x2+b*x+c, or a segmented function, which is not limited in the invention.

In the above embodiment of the invention, the property parameters of the infusion tube connected to the infusion pump are obtained, and a preset control function used to calibrate the infusion pump is determined according to the property parameters. The preset control function is configured to indicate a correlation relationship among operating parameters of the infusion pump. The plurality of sets of operating parameters of the infusion pump are obtained, and the adjustment coefficient of the infusion pump are determined according to the operating parameters according to the operating parameters and the preset control function. Then, the preset control function of the infusion pump is adjusted according to the adjustment coefficient. The method of this embodiment achieves more accurate calibration of the infusion pump by adjusting the preset control function according to determined adjustment coefficients.

Further, on the basis of the above embodiment, the process of obtaining the property parameters of the infusion tube connected to the infusion pump in the above step S101 is illustrated by the following embodiment.

The property parameters include, but are not limited to: the infusion tube material information, the tube wall thickness information, the tube inner and outer diameter information, and the tube preload amount information.

One possible implementation is as follows.

The identification information of the infusion tube input by the user is obtained.

According to the identification information, the material information, the wall thickness information, the inner-outer diameter information and the preload amount information of the infusion tube corresponding to the identification information is obtained from the pre-stored infusion tube information database.

The infusion tube material information, the tube wall thickness information, the tube inner and outer diameter information, and the tube preload amount information is obtained.

EXAMPLE

An infusion tube information library is pre-built into the infusion pump, which includes a plurality of different types of infusion tubes and parameter information associated with the infusion tubes.

The user can enter the identification information of the infusion tube connected to the infusion pump on an input interface of the infusion pump, or on a terminal that can interact with the infusion pump, so that the identification information is obtained.

According to the identification information input by the user, an infusion tube corresponding to the identification information is matched in the infusion tube information database, and the infusion tube material information, the tube wall thickness information, the tube inner and outer diameter information, and the tube preload volume information of the infusion tube is obtained.

The other possible implementation is as follows.

The infusion pump occlusion pressure when the infusion tube is squeezed and the duration of time when the infusion tube is squeezed are measured.

A preset functional relationship between the infusion pump occlusion pressure and the duration of time is obtained. The preset functional relationship is configured to indicate a correlation among the infusion pump material information, the tube wall thickness information, the tube inner and outer diameter information, and the tube preload volume information of the infusion tube.

The measured infusion pump occlusion pressure and the duration of time are input into the preset functional relationship to obtain the infusion tube material information, the tube wall thickness information, the tube inner and outer diameter information and the tube preload volume information of the infusion tube.

The infusion tube material information, the tube wall thickness information, the tube inner and outer diameter information, and the tube preload volume information is obtained.

EXAMPLE

It is assumed that the preset functional relationship between the acquired infusion tube pressure and the duration of time is $F(t)=a*b^{c*t}+d$. where a indicates the infusion tube material information, b indicates the tube wall thickness information, c indicates the tube inner or outer diameter information, and d indicates the tube preload volume information.

If four sets of infusion pump occlusion pressures and the durations of time when the infusion tubes are squeezed are (y1, t1), (y2, t2), (y3, t3), (y4, t4) respectively, and they are assumed to follow the relationship to $F(t)=a*b^{c*t}+d$, then the values of a, b, c, and d can be determined, and the infusion tube material information, the tube wall thickness information, tube inner and outer diameter information, and the tube preload volume information is obtained.

If the user is aware of the type of the infusion tube connected to the infusion pump, this implementation can also verify whether the infusion tube connected to the infusion pump is correct.

In the above embodiment of the invention, the identification information of the infusion tube input by the user is obtained. According to the identification information, the infusion tube material information, the tube wall thickness information, the tube inner and outer diameter information, and the tube preload volume information corresponding to the identification information are obtained from the pre-stored infusion tube information library by matching. Alternatively, the infusion pump occlusion pressure and the duration of time when the infusion tube is squeezed are measured. The preset functional relationship between the infusion tube pressure and the duration of time are obtained, and the measured infusion pump occlusion pressure and the duration of time are inputted into the preset functional relationship, so as to obtain the infusion tube material information, the tube wall thickness information, the tube inner and outer diameter information, and the tube preload volume information. The property parameters of the infusion tube connected to the infusion pump obtained in the above implementation are more accurate.

Further, on the basis of the above embodiment, the process of determining the adjustment coefficient of the infusion pump according to the operating parameters and the preset control function, is illustrated by the following embodiment, as shown in FIGS. 7-10.

Figure 7:
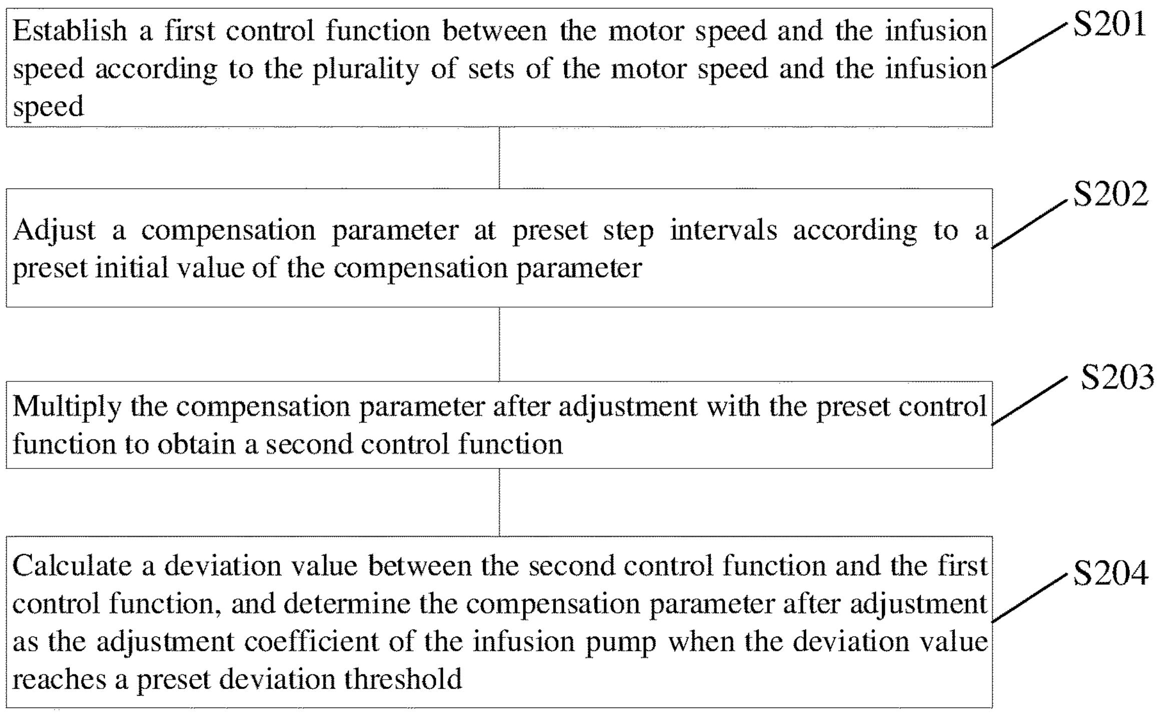
FIG. 7 shows a flowchart of a method of determining an adjustment coefficient of the infusion pump according to an embodiments of the invention.

FIG. 7 shows a flowchart of a method of determining an adjustment coefficient of an infusion pump according to an embodiment of the invention. In an embodiment, if the operating parameters are the motor speed and the infusion speed, and the preset control function is a preset control function between the motor speed of the infusion pump and the infusion speed, then the steps of the method are as follows.

- S201, a first control function between the motor speed and the infusion speed is established according to a plurality of motor speeds and infusion speeds.
- S202, a compensation parameter is adjusted at preset step intervals according to a preset initial value of the compensation parameter.
- S203, the adjusted compensation parameter is multiplied with the preset control function to obtain the second control function.
- S204, a deviation value between the second control function and the first control function is calculated, and the adjusted compensation parameter is determined as the adjustment coefficient of the infusion pump when the deviation value reaches a preset deviation threshold.

EXAMPLE

Assume that the preset control function between the motor speed of the infusion pump and the infusion speed is linear, that is, F(x)=a*x+b. A preset compensation parameter M may an initial value of, for example, 0.2, which is adjusted at preset step intervals.

First, the first control function between the motor speed and the infusion speed is established according to the motor speed and the infusion speed. It is assumed that the established first control function is F(x)=a*x+b. where x indicates the motor rotational speed and F(x) indicates the infusion speed.

The preset control function F(x)=a*x+b between the motor speed of the infusion pump and the infusion speed is multiplied with the compensation parameter M to obtain F(x)=M(a*x+b). When M=0.2, the absolute value of the difference between F(x)=M(a*x+b) and F(x)=a*x+b is calculated. If the absolute value of the difference does not satisfy a preset deviation threshold, the compensation parameter M is adjusted at preset step intervals. If the preset step to be 0.2, the current M after adjusted is 0.4. when M=0.4, the absolute value of the difference between F(x)=M(a*x+b) and F(x)=a*x+b is calculated. If the absolute value of the difference satisfies the preset deviation threshold, 0.4 is the compensation coefficient.

It should be understood that, for the above control function, the initial value of the compensation parameter, the preset step value, and the like are used for illustrative purposes only, and are not therefore to be taken as limitations on the invention.

Figure 8:
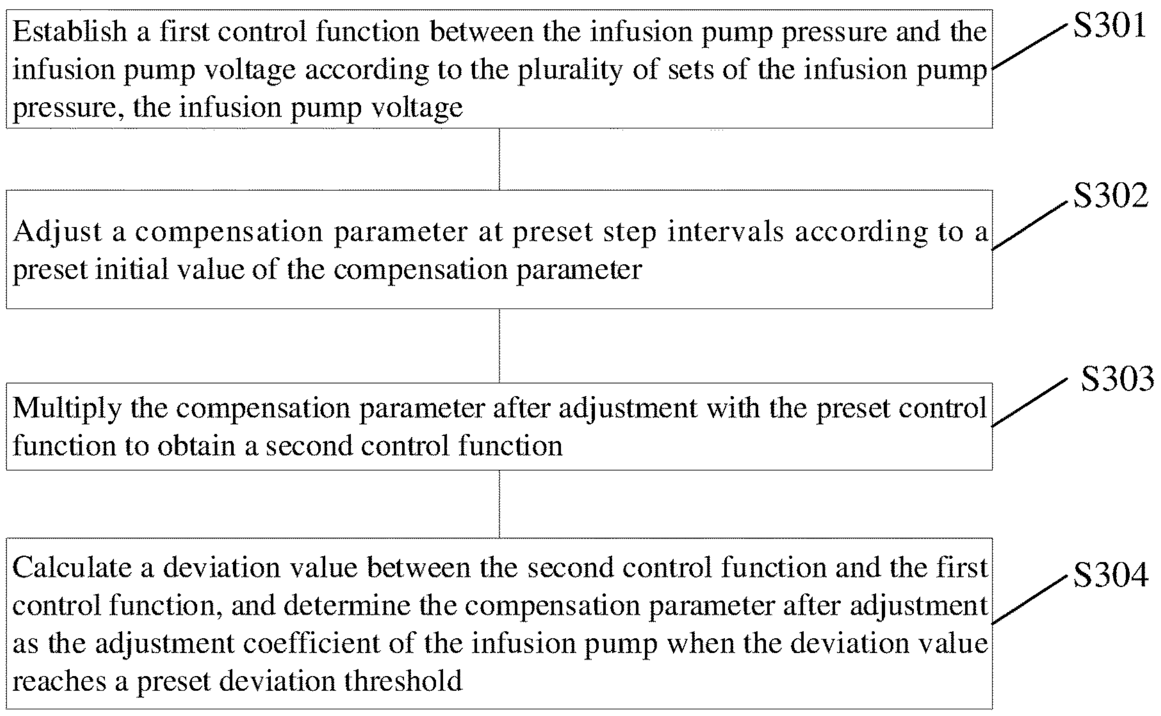
FIG. 8 shows a flowchart of another method of determining the adjustment coefficient of an infusion pump according to an embodiment of the invention.

FIG. 8 shows a flowchart of another method of determining an adjustment coefficient of an infusion pump according to an embodiment of the invention, as shown in FIG. 8.

In an embodiment, if the operating parameters are the infusion pump occlusion pressure, the infusion pump voltage, and the preset control function is a preset control function between the infusion pump occlusion pressure and the voltage of the infusion pump voltage, then the steps of the method are as follows.

- S301, a first control function between the infusion pump occlusion pressure and the infusion pump voltage is established according to a plurality of infusion pump occlusion pressures and infusion pump voltages.
- S302, a compensation parameter is adjusted at preset step intervals according to a preset initial value of the compensation parameter.
- S303, the adjusted compensation parameter is multiplied with the preset control function to obtain a second control function.
- S304, a deviation value between the second control function and the first control function is calculated, and the adjusted compensation parameter is determined as the adjustment coefficient of the infusion pump when the deviation value reaches a preset deviation threshold.

For specific examples, please refer to the portion shown in FIG. 7 above, which will not be repeated in this embodiment.

Figure 9:
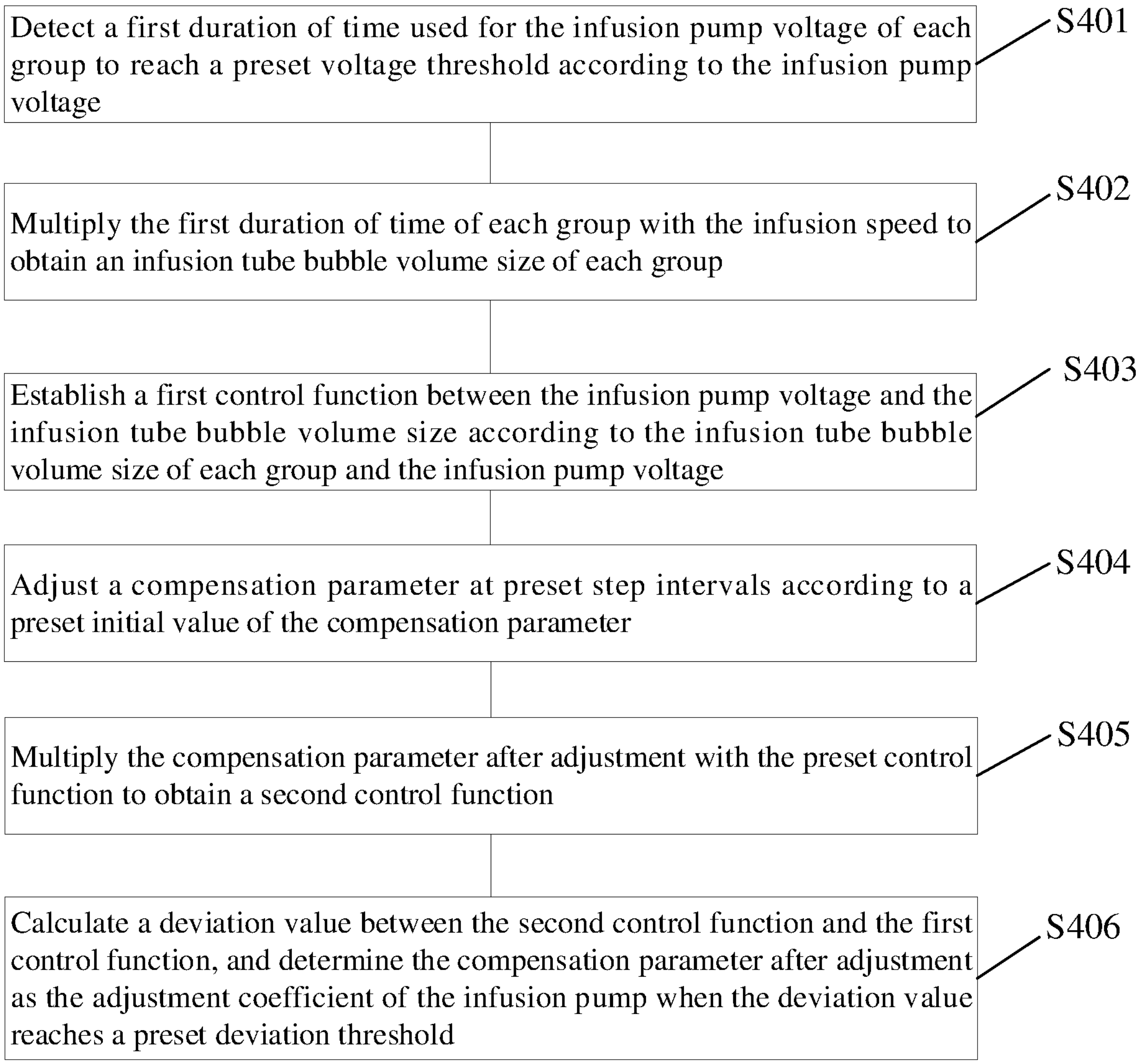
FIG. 9 shows a flowchart of yet another method of determining an adjustment coefficient of an infusion pump according to an embodiment of the invention.

FIG. 9 shows a flowchart of yet another method of determining an adjustment coefficient of an infusion pump according to an embodiment of the invention In an embodiment, if the operating parameters are the infusion rate and the infusion pump voltage, and the preset control function is a preset control function between the infusion pump voltage and a bubble volume size of the infusion tube, then the steps of the method are as follows.

- S401, the first duration of time used for the infusion pump voltage of each group to reach the preset voltage threshold is measured according to the infusion pump voltage.

S402, the first duration of time of each group is multiplied with the infusion rate to obtain the bubble volume size of the infusion tube of each group.

S403, a first control function between the infusion pump voltage and the bubble volume size of the infusion tube is established according to the multiple groups of infusion tube bubble volume sizes and infusion pump voltages.

S404, a compensation parameter is adjusted at preset step intervals according to a preset initial value of the compensation parameter.

S405, the adjusted compensation parameter is multiplied with the preset control function to obtain the second control function.

S406, a deviation value between the second control function and the first control function is calculated, and the adjusted compensation parameter is determined as the adjustment coefficient of the infusion pump when the deviation value reaches a preset deviation threshold.

Figure 10:
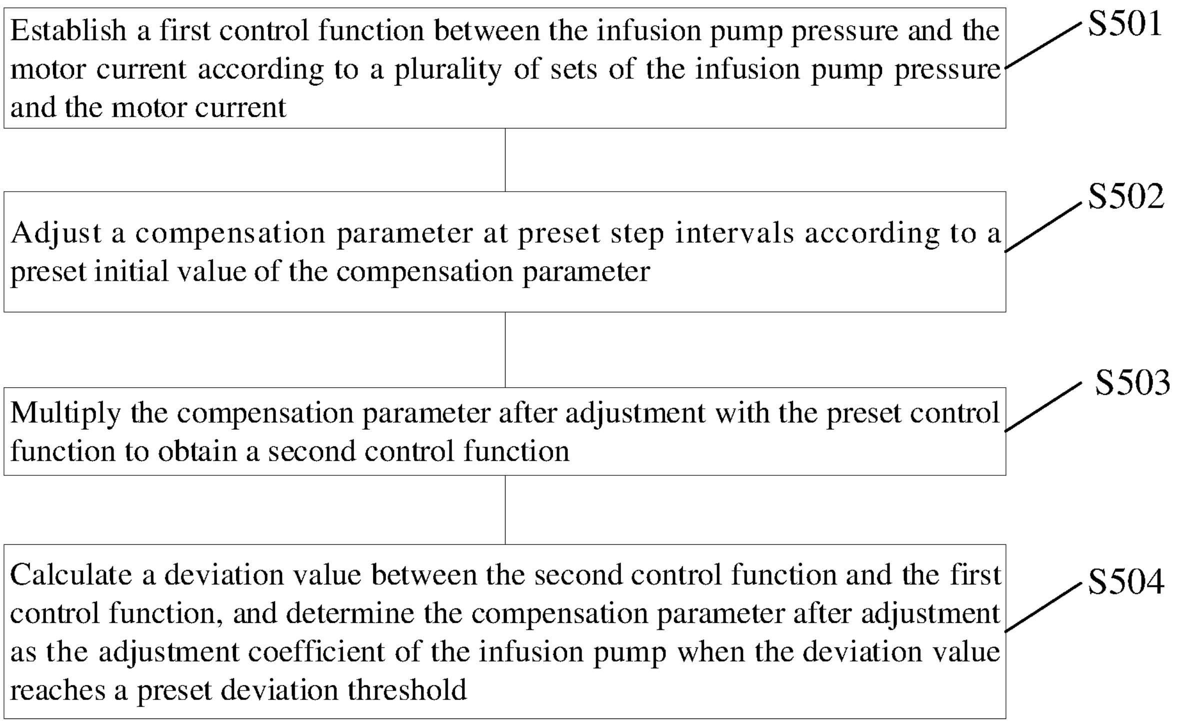
FIG. 10 shows a flowchart of yet another method of determining an adjustment coefficient of an infusion pump according to an embodiment of the invention.

FIG. 10 shows a flowchart of yet another method of determining the adjustment coefficient of the infusion pump according to an embodiment of the invention, as shown in FIG. 10.

In an embodiment, if the operating parameters are the infusion pump occlusion pressure and the motor current, and the preset control function is a preset control function between the infusion pump occlusion pressure and the motor current, then the steps of the method are as follows.

S501, a first control function between the infusion pump occlusion pressure and the motor current is established according to a plurality of infusion pump occlusion pressures and motor currents.

S502, a compensation parameter is adjusted at preset step intervals according to a preset initial value of the compensation parameter.

S503, the adjusted compensation parameter is multiplied with the preset control function to obtain the second control function.

S504, a deviation value between the second control function and the first control function is calculated, and the adjusted compensation parameter is determined as the adjustment coefficient of the infusion pump when the deviation value reaches a preset deviation threshold.

Further, after the adjustment coefficient is determined according to any of the above, the adjustment coefficient is multiplied with other preset control functions built into the infusion pump indicating the correlation between the various operating parameters, thereby obtaining the calibrated control function.

In addition, since the infusion pump also has stored a preset control function for infusion pumps connected to other types of infusion tubes, the adjustment coefficient is multiplied with this preset control function to also calibrate the preset control function for infusion pumps connected to other types of infusion tubes.

After obtaining the calibrated control function, an alarm threshold is then set according to the calibrated control function. The alarm threshold includes, but is not limited to: an infusion pump infusion rate alarm threshold, an infusion pump occlusion pressure alarm threshold, an infusion pump bubble size alarm threshold, an infusion pump motor current alarm threshold, and the like.

In the above embodiment of the invention, by determining the adjustment coefficient of the infusion pump according to the obtained operating parameters and the preset control function, so that the preset control function of the infusion pump that is adjusted more accurately according to the adjustment coefficient. The method of this embodiment improves the accuracy of the calibration results of the infusion pump.

Figure 11:
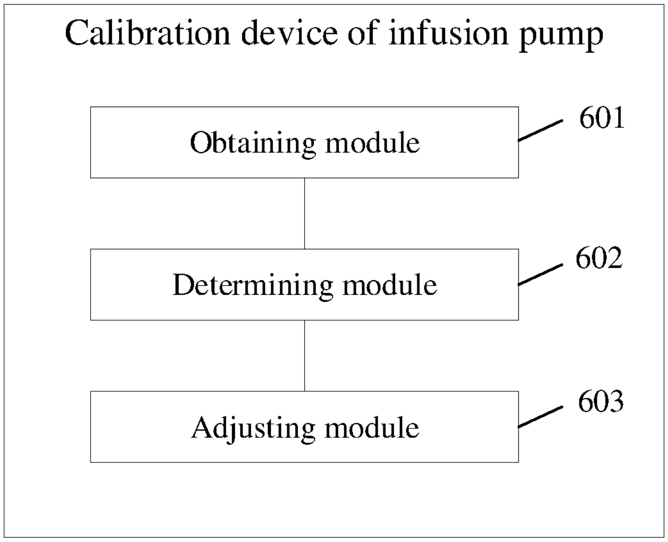
FIG. 11 shows a schematic structural diagram of a calibration device of the infusion pump according to an embodiment of the invention.
Figure 12:
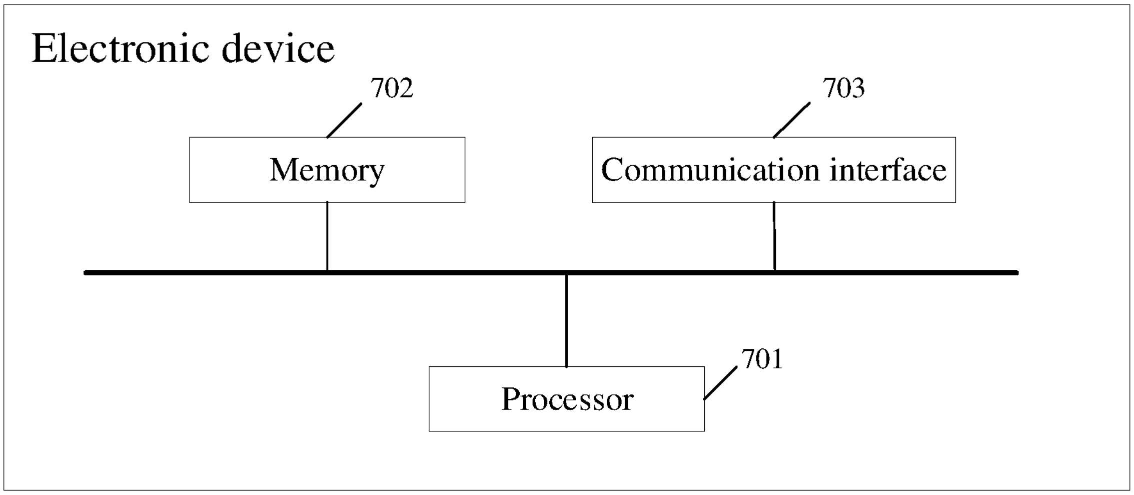
FIG. 12 shows a schematic structural diagram of an electronic device according to an embodiment of the invention.

FIG. 11 shows a schematic structural diagram of a calibration device for an infusion pump according to an embodiment of the invention. The device includes an obtaining module 601, a determination module 602, and an adjusting module 603.

The obtaining module 601 is configured to obtain property parameters of an infusion tube connected to the infusion pump.

The determination module 602 is configured to determine a preset control function used to calibrate the infusion pump according to the property parameters, in which the preset control function is configured to indicate a correlation between the operating parameters of the infusion pump.

The obtaining module 601 is further configured to obtain a plurality of sets of operating parameters of the infusion pump.

The determination module 602 is further configured to determine an adjustment coefficient of the infusion pump according to the plurality of sets of operating parameters and the preset control function.

The adjusting module 603 is configured to adjust the preset control function of the infusion pump according to the adjustment coefficient.

In one possible implementation, the determination module 602 is specifically configured to:

establish a first control function between the motor speed and the infusion rate according to a plurality of motor speeds and infusion speeds;

adjust a compensation parameter at preset step intervals according to a preset initial value of the compensation parameter;

multiply the adjusted compensation parameter with the preset control function to obtain the second control function; and calculate a deviation value between the second control function and the first control function, and when the deviation value reaches a preset deviation threshold, determine the adjusted compensation parameter as the adjustment coefficient of the infusion pump.

In one possible implementation, the determination module 602 is specifically configured to:

establish a first control function between the infusion pump occlusion pressure and the infusion pump voltage according to a plurality of infusion pump occlusion pressures and infusion pump voltages;

adjust a compensation parameter at preset step intervals according to a preset initial value of the compensation parameter;

multiply the adjusted compensation parameter with the preset control function to obtain a second control function; and calculate a deviation value between the second control function and the first control function, and when the deviation value reaches a preset deviation threshold, determine the adjusted compensation parameter as the adjustment coefficient of the infusion pump.

In one possible implementation, the determination module 602 is specifically configured to:

measure the first duration of time used for the infusion pump voltage of each group to reach the preset voltage threshold according to the infusion pump voltage;

multiply the first duration of time of each group with the infusion speed to obtain the bubble volume size of the infusion tube of each group;

establish a first control function between the infusion pump voltage and the bubble volume size of the infusion tube according to the bubble volume size of the infusion tubes and the infusion pump voltages of the various groups.

adjust the compensation parameter at preset step intervals according to a preset initial value of the compensation parameter;

multiply the adjusted compensation parameter with the preset control function to obtain a second control function.

calculate a deviation value between the second control function and the first control function, and when the deviation value reaches a preset deviation threshold, determine the adjusted compensation parameter as the adjustment coefficient of the infusion pump.

In one possible implementation, the determination module 602 is specifically configured to:

establish a first control function between the infusion pump occlusion pressure and the motor current according to a plurality of infusion pump occlusion pressures and motor currents;

adjust the compensation parameter at preset step intervals according to a preset initial value of the compensation parameter;

multiply the adjusted compensation parameters with the preset control function to obtain the second control function; and calculate a deviation value between the second control function and the first control function, and when the deviation value reaches the preset deviation threshold, determine the adjusted compensation parameter as the adjustment coefficient of the infusion pump.

In one possible implementation, the obtaining module 601 is specifically configured to:

measure the motor speed of the infusion pump, the infusion pump occlusion pressure, the infusion pump voltage, and the motor current of the infusion pump;

measure the infusion rate of the infusion pump, or, measure a liquid volume in the infusion tube connected to the infusion pump, and the second duration of time used for the liquid to flow through the infusion tube, and divide the liquid volume with the second duration of time to obtain the infusion rate; and obtain a plurality of motor speeds of the infusion pump, the infusion rates, the infusion pump occlusion pressures, the infusion pump voltages and the infusion pump motor currents.

In one possible implementation, the obtaining module 601 is specifically configured to:

obtain identification information of the infusion tube entered by the user;

obtain the infusion tube material information, the tube wall thickness information, the tube inner and outer diameter information, and the tube preload amount information of the infusion tube corresponding to the identification information from the pre-stored infusion tube information library by matching according to the identification information; and obtain the infusion tube material information, the tube wall thickness information, the tube inner and outer diameter information, and the tube preload amount information.

In one possible implementation, the obtaining module 601 is specifically configured to:

measure the infusion pump occlusion pressure when the infusion tube is squeezed, and the third duration of time when the infusion tube is squeezed;

obtain a preset functional relationship between the infusion tube pressure and the duration of time, in which the preset functional relationship is configured to indicate a correlation among the infusion tube material information, the tube wall thickness information, the tube inner and outer diameter information, and the tube preload volume information of the infusion tube;

input the measured infusion pump occlusion pressure and the third duration of time into the preset functional relationship to obtain the infusion tube material information, the tube wall thickness information, the tube inner and outer diameter information, and the tube preload volume information of the infusion tube; and obtain the infusion tube material information, the tube wall thickness information, the tube inner and outer diameter information, and the tube preload volume information.

The calibration device of the infusion pump provided in this embodiment is configured to perform the above-mentioned method embodiments. Its underlying principle and technical effect are analogous, which will not be further described herein.

FIG. 11 is a schematic structural diagram of an electronic device according an embodiment of the invention. As shown in FIG. 11, the electronic device may include at least one processor 701 and a memory 702. The processor 701 may be configured to act as the controller; in other embodiments, the calibration device may be configured as the controller. The device in which the code that the controller executes to perform its described functions may be chosen according to the preference of the system designer.

The memory 702 is configured to store a program. Specifically, the program may include program code, which includes computer operation instructions.

The memory 702 may include a high-speed RAM memory, or may also include a non-volatile memory, such as at least one disk memory.

The processor 701 is configured to execute the computer operation instructions stored in the memory 702 to implement the methods described in the preceding embodiments. The processor 701 may be a Central Processing Unit (CPU), or an Application Specific Integrated Circuit (ASIC), or one or more integrated circuits configured to implement embodiments of the invention.

In an embodiment, the electronic device may further include a communication interface 703. In a specific implementation, if the communication interface 703, the memory 702, and the processor 701 are implemented independently, the communication interface 703, the memory 702, and the processor 701 may be connected to each other through a bus and complete communication with each other. The bus may be an Industry Standard Architecture (ISA) bus, a Peripheral Component (PCI) bus, or an Extended Industry Standard Architecture (EISA) bus and so on. Buses may be classified as address buses, data buses, control buses, etc., but It does not mean that there is only one bus or one type of bus.

In an embodiment, if the communication interface 703, the memory 702, and the processor 701 are integrated and implemented on a single chip, the communication interface 703, the memory 702, and the processor 701 may complete the communication through an internal interface.

This embodiment provides an electronic device for performing the aforementioned calibration method of the infusion pump. Its underlying principle and technical effect are analogous, which will not be further described herein.

The invention further provides a computer-readable storage medium, the computer-readable storage medium may include: a USB flash drive, a mobile hard disk, a read-only memory (ROM), a random access memory (RAM), a magnetic disk, a compact disc, or other kinds of media that can store program code. Specifically, the computer-readable storage medium stores program instructions, and the program instructions is configured to implement the above-mentioned calibration method of the infusion pump.

The invention further provides a computer program product, which includes executable instructions. The executable instructions is stored in the computer-readable storage medium. At least one processor of the electronic device can read the executable instructions from the readable storage medium, and the at least one processor executes the executable instructions causing the electronic device to implement the above-mentioned calibration method of the infusion pump provided by the various embodiments described above.

Other embodiments of the invention will readily come to mind to those skilled in the art upon consideration of the specification and practice of the invention disclosed herein. The invention is intended to cover any variations, uses, or adaptations of the invention that follow the general principles of the invention and include common knowledge or customary technical means in the art not disclosed herein. The specification and embodiments are to be regarded as exemplary only, and the true scope and spirit of this application is indicated by the following claims.

It should be understood that the invention is not limited to the precise structure described above and illustrated in the accompanying drawings. Various modifications and alterations may be made within the scope of the invention without departing from its essence. The scope of the invention is limited only by the appended claims.

The invention claimed is:

1. A control method of an infusion pump, comprising:

determining at least one of identification information or consumable information of a target infusion consumable mounted in the infusion pump, said target infusion consumable comprising a tube configured to deliver a fluid;

determining, according to the at least one of identification information or consumable information, a control rule corresponding to the target infusion consumable of the infusion pump;

adjusting the control rule corresponding to the target infusion consumable according to a preset correction rule; and operating the infusion pump according to the control rule.

2. The method of claim 1, wherein the control rule is a function of at least one physical property of the tube and comprises at least one of: an infusion accuracy control rule, a blocking pressure control rule, a bubble judgment rule, and a drive mechanism current adjustment rule.

3. The method of claim 1, wherein the step of determining at least one of identification information or consumable information of the target infusion consumable mounted in the infusion pump comprises:

determining the at least one of identification information or consumable information of the target infusion consumable by at least one of a consumable identification device or an interaction device in communication with the infusion pump.

4. The method of claim 1, wherein the step of adjusting the control rule corresponding to the target infusion consumable according to the preset correction rule, comprises:

obtaining feedback information of the infusion pump for a preset time period; wherein the feedback information comprising fluid information of the infusion pump;

determining, according to the feedback information, the preset correction rule, and adjusting the control rule of the target infusion consumable according to the preset correction rule.

5. The method of claim 4, further comprising:

determining a plurality of control rules for the target infusion consumable;

determining, according to the feedback information, the preset correction rule and adjusting the control rule of the target infusion consumable according to the preset correction rule, by:

determining, according to the feedback information, a preset correction rule corresponding to a first control rule of the target infusion consumable; and adjusting at least one control rule of the target infusion consumable according to the preset correction rule of the first control rule.

6. The method of claim 4, further comprising:

determining for the infusion pump a plurality of control rules for a plurality of infusion consumables stored therein, adjusting a control rule of at least one other type of infusion consumable stored within the infusion pump according to the preset correction rule.

7. The method of claim 4, wherein the step of obtaining feedback information from the infusion pump for the preset time period is followed by:

determining, according to the feedback information, actual consumable information of the target infusion consumable.

8. The method of claim 1, wherein the method further comprises:

updating the control rule of the target infusion consumable.

9. A control method of an infusion pump, comprising:

determining a control rule of a target infusion consumable mounted in the infusion pump, said target infusion consumable comprising a tube configured to deliver a fluid;

operating the infusion pump according to the control rule, and obtaining feedback information of the infusion pump for a preset time period, wherein the feedback information comprises fluid information of the infusion pump;

determining, according to the feedback information, actual consumable information of the target infusion consumable.

10. The method of claim 9, wherein the control rule is a function of at least one physical property of the tube and comprises at least one of: an infusion accuracy control rule, a blocking pressure control rule, a bubble judgment rule, and a drive mechanism current adjustment rule.

11. The method of claim 9, wherein a plurality of preset consumable information and identification information of an infusion consumable associated with each of the preset consumable information are stored in the infusion pump; the method further comprising:

comparing the actual consumable information with the plurality of preset consumable information stored in the infusion pump to determine identification information for the target infusion consumable.

12. The method of claim 11, wherein the method further comprises:

outputting the identification information of the target infusion consumable.

13. The method of claim 9, further comprising:

storing in the infusion pump identification information of a plurality of infusion consumables and preset consumable information associated with each of the identification information;

obtaining the identification information of the target infusion consumable;

determining, according to the identification information, preset consumable information associated with the identification information; and calculating a deviation value between the actual consumable information and the preset consumable information, and issuing an alarm prompt when the deviation value reaches a preset deviation threshold.

14. The method of claim 9, further comprising:

determining the actual consumable information of the target infusion consumable; and adjusting a control rule stored within the infusion pump associated with the actual consumable information.

15. An infusion pump, comprising:

a controller, a drive mechanism, an extrusion member and an infusion consumable, said infusion consumable comprising a tube mounted in the infusion pump and configured to deliver a fluid;

wherein the controller is connected to the drive mechanism, the drive mechanism is connected to the extrusion member in a drive connection, and the extrusion member is disposed on a tube wall of the infusion consumable;

the controller is configured to cause the infusion pump to perform a control method of an infusion pump, the controller being further configured:

to determine at least one of identification information or consumable information of a target infusion consumable mounted in the infusion pump;

to determine, according to the at least one of identification information or consumable information, a control rule corresponding to the target infusion consumable of the infusion pump; and to adjust the control rule corresponding to the target infusion consumable according to a preset correction rule.

16. The infusion pump of claim 15, wherein the controller is further configured to determine the at least one of identification information and consumable information of the target infusion consumable mounted in the infusion pump by determining the at least one of identification information or consumable information of the target infusion consumable by at least one of a consumable identification device or an interaction device in communication with the infusion pump.

17. The infusion pump of claim 15, wherein the controller is further configured to adjust the control rule corresponding to the target infusion consumable according to the preset correction rule, by:

operating the infusion pump according to the control rule corresponding to the target infusion consumable;

obtaining feedback information of the infusion pump for a preset time period; wherein the feedback information comprising fluid information of the infusion pump;

determining, according to the feedback information, the preset correction rule, and adjusting the control rule of the target infusion consumable according to the preset correction rule.

18. The infusion pump of claim 15, wherein the target infusion consumable is associated with a plurality of control rules;

the controller is further configured to determine, according to the feedback information, the preset correction rule and adjusting the control rule of the target infusion consumable according to the preset correction rule, by:

determining, according to the feedback information, a preset correction rule corresponding to a first control rule of the target infusion consumable;

adjusting at least one control rule of the target infusion consumable according to the preset correction rule of the first control rule.

19. The infusion pump of claim 15, wherein the infusion pump is in communication with a storage device that stores a plurality of control rules for a plurality of infusion consumables, the controller being further configured to adjust a control rule of at least one other type of infusion consumable stored within the infusion pump according to the preset correction rule.

20. The infusion pump of claim 15, wherein the controller is further configured to update the control rule of the target infusion consumable.

* * * * *